United States Patent
Simons et al.

(10) Patent No.: US 12,059,337 B2
(45) Date of Patent: Aug. 13, 2024

(54) SURGICAL TEXTILE WITH BARBS AND LOOPS

(71) Applicant: Sofradim Production, Trévoux (FR)

(72) Inventors: Damien Simons, Trevoux (FR); Nizar Bechir, Trevoux (FR); Thierry Brune, Trevoux (FR)

(73) Assignee: SOFRADIM PRODUCTION, Trevoux (FR)

( * ) Notice: Subject to any disclaimer, the term of this patent is extended or adjusted under 35 U.S.C. 154(b) by 383 days.

(21) Appl. No.: 17/230,971

(22) Filed: Apr. 14, 2021

(65) Prior Publication Data

US 2021/0322145 A1 Oct. 21, 2021

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *A61F 2002/0068* (2013.01); *A61F 2210/0004* (2013.01); *A61F 2220/0016* (2013.01); *D10B 2501/0632* (2013.01); *D10B 2509/08* (2013.01)

(58) Field of Classification Search
CPC ............ A61F 2/0063; A61F 2002/0068; A61F 2210/0004; A61F 2220/0016; D04B 21/12; D10B 2501/0632; D10B 2509/08
See application file for complete search history.

(56) References Cited

U.S. PATENT DOCUMENTS

| | | |
|---|---|---|
| 3,320,649 A | 5/1967 | Naimer |
| 3,718,725 A | 2/1973 | Hamano |
| 4,259,959 A * | 4/1981 | Walker ............... A61B 17/08 606/221 |
| 4,338,800 A | 7/1982 | Matsuda |
| 4,391,106 A | 7/1983 | Schaefer et al. |
| 4,476,697 A | 10/1984 | Schafer et al. |
| 4,709,562 A | 12/1987 | Matsuda |
| 5,254,127 A | 10/1993 | Wholey et al. |
| 5,254,133 A | 10/1993 | Seid |

(Continued)

FOREIGN PATENT DOCUMENTS

| | | |
|---|---|---|
| DE | 19832634 A1 | 1/2000 |
| EP | 0276890 A2 | 8/1988 |

(Continued)

OTHER PUBLICATIONS

Extended European Search Report issued in European Application No. 21168409.7 dated Aug. 23, 2021, 6 pages.

*Primary Examiner* — Jing Rui Ou (74) *Attorney, Agent, or Firm* — Weber Rosselli & Cannon LLP (57) ABSTRACT

The present invention relates to a surgical textile (1) comprising an arrangement of biocompatible yarns defining a first face (2) and a second face (3) of the textile, the second face opposite the first face, the textile being provided at least on an area of a surface of one of its faces with a plurality of barbs (4) showing substantially a first length L1, measured perpendicularly to that surface, characterised in that said area of said surface is further provided with a plurality of loops (5), said loops showing substantially a second length L2, measured perpendicularly to that surface, where L2 is greater than L1. The invention further relates to a process for manufacturing such a textile.

18 Claims, 8 Drawing Sheets

(56) References Cited

U.S. PATENT DOCUMENTS

| | | | |
|---|---|---|---|
| 5,330,445 A | 7/1994 | Haaga | |
| 5,356,432 A | 10/1994 | Rutkow et al. | |
| 5,515,583 A * | 5/1996 | Higashinaka | A44B 18/003 |
| | | | 24/448 |
| 5,569,273 A | 10/1996 | Titone et al. | |
| 5,761,775 A | 6/1998 | Legome et al. | |
| 5,906,617 A | 5/1999 | Meislin | |
| 6,039,741 A | 3/2000 | Meislin | |
| 6,110,210 A | 8/2000 | Norton et al. | |
| 6,120,539 A | 9/2000 | Eldridge et al. | |
| 6,408,656 B1 | 6/2002 | Ory et al. | |
| 6,443,964 B1 | 9/2002 | Ory et al. | |
| 6,596,002 B2 | 7/2003 | Therin et al. | |
| 6,638,284 B1 | 10/2003 | Rousseau et al. | |
| 6,971,252 B2 | 12/2005 | Therin et al. | |
| 6,991,643 B2 * | 1/2006 | Saadat | A61F 2/4618 |
| | | | 606/221 |
| 7,083,637 B1 | 8/2006 | Tannhauser | |
| 7,213,421 B2 | 5/2007 | Shirasaki et al. | |
| 7,275,290 B2 | 10/2007 | Clarner et al. | |
| 7,331,199 B2 | 2/2008 | Ory et al. | |
| 7,614,258 B2 | 11/2009 | Cherok et al. | |
| 9,445,883 B2 | 9/2016 | Lecuivre et al. | |
| 9,750,593 B2 * | 9/2017 | Meneghin | A61F 2/0063 |
| 9,839,504 B2 | 12/2017 | Miller et al. | |
| 9,839,505 B2 | 12/2017 | Romuald et al. | |
| 10,080,639 B2 * | 9/2018 | Lecuivre | D04B 21/12 |
| 10,349,707 B2 | 7/2019 | Verstraete et al. | |
| 2004/0039453 A1 | 2/2004 | Anderson et al. | |
| 2004/0073235 A1 | 4/2004 | Lund et al. | |
| 2004/0163221 A1 * | 8/2004 | Shepard | A44B 18/0011 |
| | | | 24/452 |
| 2004/0225181 A1 | 11/2004 | Chu et al. | |
| 2006/0281967 A1 | 12/2006 | Meneghin et al. | |
| 2007/0032695 A1 | 2/2007 | Weiser | |
| 2007/0038018 A1 | 2/2007 | Chu et al. | |
| 2007/0043255 A1 | 2/2007 | O'donnell | |
| 2008/0081945 A1 | 4/2008 | Toso et al. | |
| 2008/0161837 A1 | 7/2008 | Toso et al. | |
| 2008/0195231 A1 | 8/2008 | Ory et al. | |
| 2008/0208360 A1 | 8/2008 | Meneghin et al. | |
| 2008/0269548 A1 | 10/2008 | Vecchiotti et al. | |
| 2009/0036907 A1 | 2/2009 | Bayon et al. | |
| 2010/0049222 A1 | 2/2010 | Cherok et al. | |
| 2010/0299880 A1 | 12/2010 | Pezzoli | |
| 2010/0312043 A1 | 12/2010 | Goddard | |
| 2011/0230707 A1 | 9/2011 | Roll et al. | |
| 2013/0052403 A1 * | 2/2013 | Barker | A44B 18/0023 |
| | | | 26/9 |
| 2013/0172915 A1 * | 7/2013 | Thomas | A61F 2/0063 |
| | | | 606/151 |
| 2014/0094829 A1 * | 4/2014 | Kostrzewski | A61F 2/0063 |
| | | | 606/151 |
| 2014/0350578 A1 * | 11/2014 | Lecuivre | D04B 21/14 |
| | | | 28/165 |

FOREIGN PATENT DOCUMENTS

| | | |
|---|---|---|
| EP | 0719527 A1 | 7/1996 |
| EP | 0797962 A2 | 10/1997 |
| EP | 0827724 A2 | 3/1998 |
| EP | 0836838 A1 | 4/1998 |
| EP | 2229918 A1 | 9/2010 |
| EP | 2514862 A2 | 10/2012 |
| EP | 2473214 B1 | 3/2014 |
| EP | 2473133 B1 | 4/2014 |
| FR | 2744906 A1 | 8/1997 |
| FR | 2766698 A1 | 2/1999 |
| FR | 2779937 A1 | 12/1999 |
| WO | 9507666 A1 | 3/1995 |
| WO | 9603091 A1 | 2/1996 |
| WO | 9641588 A1 | 12/1996 |
| WO | 0181667 A1 | 11/2001 |
| WO | 03092546 A2 | 11/2003 |
| WO | 03105727 A1 | 12/2003 |
| WO | 2012021600 A1 | 2/2012 |
| WO | 2013020076 A1 | 2/2013 |
| WO | 2013026682 A1 | 2/2013 |
| WO | 2013098345 A1 | 7/2013 |

\* cited by examiner

SURGICAL TEXTILE WITH BARBS AND LOOPS

CROSS-REFERENCE TO RELATED APPLICATIONS

This application claims benefit of and priority to French Patent Application Serial No. FR2003833 filed Apr. 16, 2020, the disclosure of the above-identified application is hereby incorporated by reference in its entirety.

The present invention relates to a surgical textile provided at least on one of its faces with barbs and loops, the barbs being capable of being deactivated when the surgical textile is conveyed to an implantation site. Such a textile can particularly be used for producing tissue-reinforcing prostheses intended to be introduced into a patient, either by a classical open surgery route or by minimally invasive surgery.

Tissue-reinforcing prostheses, for example prostheses for reinforcing the abdominal wall, are widely used in the surgical field. These prostheses are intended to treat hernias by temporarily or permanently filling a tissue defect. These prostheses are generally made of biocompatible prosthetic fabric and can have a number of shapes, for example rectangular, circular or oval, depending on the anatomical structure to which they are to be fitted. Some of these prostheses are made from entirely bioresorbable yarns and are intended to disappear after having carried out their reinforcing role while cell colonization takes place and tissue rehabilitation takes over. Other prostheses comprise non-biodegradable yarns and are intended to remain permanently in the body of the patient.

Some of these prostheses comprise an arrangement of yarns, such as a knit, a woven fabric or non-woven fabric, comprising barbs that protrude outwards from one face, sometimes from the two faces, of the prosthesis: these barbs constitute hooks that are able to fix themselves either in another prosthetic fabric, belonging to the same prosthesis or not, or directly in the biological tissues, for example the abdominal wall.

The presence of barbs on at least one face of a surgical textile to be implanted in a patient has therefore the advantage of enabling the surgical textile to directly grip to the biological tissue, so that it is possible to fix the surgical textile without having to use conventional attaching means such as staples, sutures, which may be traumatizing for the biological tissues and which may in addition cause tensions in the biological tissues and/or cause tearing in the textile.

Anyway, surgical textiles with barbs may also leave the surgeon with some negative perceptions, those negative perceptions making such surgical textiles challenging to implant.

Indeed, when the surgical textile with barbs is conveyed to the implantation site, it may happen that the barbs stick to the tissues adjacent the implantation site, making it difficult to bring the surgical textile up to the implantation site without possibly damaging the adjacent tissues, and/or the surgical textile itself. The introduction phase of the surgical textile is therefore not rendered comfortable for the surgeon.

Furthermore, for the sake of minimizing the traumatisms subsequent to any surgical operation, patients are increasingly often operated on via minimally invasive surgery when the type of operation carried out permits it. Minimally invasive surgery requires only very small incisions, through which a trocar is passed, within which the prosthesis is conveyed to the implantation site. An advantage of minimally invasive surgery is that open surgery is avoided, allowing the patient to leave hospital rapidly. Minimally invasive surgery is particularly popular in surgical operations carried out in the abdomen, such as for example the treatment of hernias.

However, the trocars used in minimally invasive surgery generally have a relatively small calibrated diameter, which may vary, for example, from 5 to 15 mm, in order to reduce the size of the incision made as much as possible. The prosthesis must therefore be conveyed within a channel of reduced diameter and it must then be deployed at the implantation site.

In order to carry out this step, the prosthesis is generally rolled up on itself in order to make it slide in the channel of the trocar or directly introduced by force. However, when the surgical textile forming the prosthesis comprises barbs at least on one face, it may happen that these barbs become entangled in the body of the textile and hinder the subsequent deployment of the prosthesis at the implantation site. Deploying and spreading out the surgical textile on the implantation site may therefore constitute a challenge for the surgeon. Furthermore, due to the fact that they are not protected, the barbs may be damaged during the unrolling of the surgical textile or during its transportation through the trocar to the implantation site.

Another drawback that may be encountered with surgical textiles having barbs is that the barbs make the textile difficult to reposition once on the implantation site. Indeed, once a surgical textile is conveyed up to an implantation site, it may happen that the surgeon wishes to try various locations and/or positioning of the textile with regards to the surrounding tissues so that the textile is able to ensure its function properly once fixed. The fact that the barbs make it difficult to detach and re-attach the textile to tissues may render this positioning step challenging for the surgeon.

Thus, there remains a need for a surgical textile provided with barbs, where such surgical textile would be capable of being introduced in the body of the patient without damaging the barbs and/or the surrounding biological tissues by sticking to said tissues, and would further be capable of being easily spread out, and repositioned when required, and preferably in an easy way, once said surgical textile has reached the implantation site.

An aspect of the invention is a surgical textile provided with barbs, said surgical textile being further provided with means capable of deactivating the barbs before said barbs have to play their gripping function.

The invention relates to a surgical textile comprising an arrangement of biocompatible yarns defining a first face and a second face of the textile, the second face opposite the first face, the textile being provided at least on an area of a surface of one of its faces with a plurality of barbs showing substantially a first length L1, measured perpendicularly to that surface, characterised in that said area of said surface is further provided with a plurality of loops, said loops showing substantially a second length L2, measured perpendicularly to that surface, where L2 is greater than L1.

The barbs of the surgical textile according to the invention may protrude from a face of the textile substantially perpendicularly to the plane of said face or alternatively along one or more planes that are inclined relative to the plane of said face. These barbs are intended to function as fastening means, either by becoming entangled in one or more arrangements of yarns, fibres, filaments and/or multifilaments of another prosthetic fabric, for example in order to form a composite reinforcing prosthesis, or by anchoring directly in the biological tissues, such as for example an abdominal wall, once the prosthesis comprising this surgical textile or constituted of this surgical textile is implanted.

In the present document, the perpendicular lengths of the barbs L1 and of the loops L2 are measured from the surface of the face of the textile from which they protrude, as the distance between that surface and the furthest point of the barb or of the loop from that surface, along a perpendicular line to that surface. The true length of the barbs, i.e. the distance between the foot of the barb and its head along a longitudinal axis of the barb, and the true length of the loops, i.e. the distance between the basis of the loop and its apex along a longitudinal axis of the loop, may be different from their respective perpendicular lengths as defined above. Indeed, in the surgical textile of the invention, the barbs and/or the loops may extend perpendicularly to the surface of the face of the textile, in which case their perpendicular lengths are substantially identical to their true lengths, but they also alternatively may extend obliquely from that surface, in which case their perpendicular lengths is smaller than their true lengths.

The surgical textile of the invention allows deactivating the barbs before they have to grip another fabric or the biological tissue at the implantation site.

Indeed, the loops of the textile of the invention allow protecting the barbs while the textile is conveyed to the implantation site. During the time the textile is moved within the surrounding tissues, the loops, because of their perpendicular length L2 being greater than the barbs' perpendicular length L1, prevent the barbs to anchor into the tissues. The gripping function of the barbs is therefore deactivated.

Once the surgical textile has reached the implantation site, it is positioned so that the face of the textile provided with the barbs and the loops faces the biological tissues to which the textile is intended to be fixed. The surgeon may then apply a pressure on the face of the textile opposite the face provided with the barbs and the loops. The pressure thus applied on the textile in the direction of the biological tissue will cause the loops to flatten, and the barbs will protrude outwards and will be able to grip said biological tissue. The gripping function of the barbs is therefore activated.

In particular, in the use of the surgical textile of the invention, the barbs may be deactivated during the introduction of the textile in the body of the patient, during the deployment of the textile and during the potential repositioning of the textile: all these steps are therefore rendered easier to perform for the surgeon. Moreover, the barbs may be activated only when the surgeon feels the need to do so, for example when he feels the textile is a the right position, simply by applying a pressure on the textile: such a step is also easy to perform.

In embodiments, L2 may be from 20% to 140% longer than L1, preferably from 40% to 100% longer than L1. For example, L2 may be 80% longer than L1. For example, L1 may range from 0.5 mm to 1.0 mm, preferably from 0.7 mm to 0.9 mm, and L2 may range from 0.8 mm to 1.2 mm, preferably from 0.9 mm to 1.1 mm.

The barbs and the loops of the surgical textile of the invention are made of biocompatible material. For example, the barbs and the loops are made of yarns or of yarn cuts, for example of yarns of said arrangement of yarns. The barbs and the loops may be made of the same yarns or of different yarns.

For example, in embodiments, the barbs are made of a yarn having a diameter D1 and the loops are made of a yarn having a diameter D2, where D1 is greater than D2.

Such embodiments allow providing a surgical textile for which the force to apply to anchor the barbs into a biological tissue or other fabric may be moderate. Indeed, the fact that D2 is smaller than D1 allows obtaining barbs that show a significant strength or rigidity while the loops show a moderate spring effect. The risk that the textile uplifts due to the presence of the loops is therefore reduced. The activation of the barbs is facilitated since the force necessary to reduce/flatten the loops may be reduced.

In embodiments, D1 may be from 10% to 80% greater than D2, preferably from 15% to 40% greater than the diameter D2. For example, D1 may be 25% greater than D2.

D1 may range from 0.10 mm to 0.18 mm, preferably from 0.11 mm to 0.16 mm, and D2 may range from 0.09 mm to 0.17 mm, preferably from 0.10 mm to 0.15 mm.

In other embodiments, for example, the barbs are made of a yarn having a diameter D3 and the loops are made of a yarn having a diameter D4, where D4 is greater than D3.

Such embodiments allow providing a surgical textile particularly efficient for avoiding that the barbs anchor the surrounding biological tissues before the surgical textile reaches the implantation site. Indeed, the fact that the diameter D4 is greater than D3 produces stiffer loops that ensure that the barbs are prevented from gripping to the biological tissues before the surgeon actually decides it. The deactivation of the barbs is therefore particularly efficient, and the barbs do not penetrate the tissue or another fabric before the surgeon decides to apply the necessary pressure on the textile.

In embodiments, D4 may be from 10% to 80% greater than D3, preferably from 15% to 40% greater than D3.

D4 may range from 0.10 mm to 0.18 mm, preferably from 0.11 mm to 0.16 mm, and D3 may range from 0.09 mm to 0.17 mm, preferably from 0.10 mm to 0.15 mm.

The yarns of the textile of the invention are yarns of biocompatible material which may or may not be biodegradable.

In the present application, "biocompatible" is understood as meaning that the materials having this property can be implanted in the human or animal body.

All biocompatible materials may be synthetic or natural, biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

The yarns forming the first and second faces of the textile, the loops and the barbs may be made of any biodegradable or non-biodegradable biocompatible material. Thus, the biodegradable materials suitable for the yarns forming the first and second faces of the textile, the loops and the barbs of the surgical textile of the present invention may be selected from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers thereof and mixtures thereof. The non-biodegradable materials suitable for the yarns forming the first and second faces of the textile, the loops and the barbs of the surgical textile of the present invention may be selected from polyethylene terephthalate (PET), polyamides, aramids, expanded polytetrafluoroethylene, polyurethane, polyvinylidene difluoride (PVDF), butyl ester polymers, polyetheretherketone (PEEK), polyolefins (such as polyethylene or polypropylene), polyethers, copper alloys, silver or platinum alloys, medical grades of steel such as medical-grade stainless steel, and combinations thereof.

In embodiments, the barbs are made of a biodegradable material. Such embodiments allow providing a surgical textile that limits the introduction of foreign material in the body of the patient. Once the surgical textile is colonized by the biological tissue and the gripping function of the barbs is no more necessary, the barbs are biodegraded.

In embodiments, the barbs are made of heat-fusible monofilament yarn cuts. For example, the heat-fusible monofilament yarn cuts are made of polylactic acid monofilament yarn having a diameter of 0.15 mm: such a yarn having such a diameter makes it possible to obtain barbs that have good anchoring abilities in biological tissues or in another openwork fabric.

The yarns forming the first and second faces of the textile constitute the ground structure of the surgical textile, in other words the background of the textile, and they may be selected from monofilament yarns, multifilament yarns and combinations thereof. The yarns forming the first and second faces of the textile may be identical or different from the yarns forming the loops and the barbs.

In embodiments, the yarns forming the first and second faces of the textile are monofilament yarns made of polyester terephthalate (PET) having a diameter of 0.09 mm.

In embodiments, the yarns forming the loops are monofilament yarns made of polylactic acide (PLA) having a diameter of 0.15 mm. Such yarns have an intrinsic stiffness allowing obtaining stiffer loops.

In embodiments, the arrangement of yarns of the surgical textile of the invention is a knit comprising i) one or more yarn(s) forming the first and second faces of the textile and the loops and ii) heat-fusible monofilament yarn cuts forming the barbs.

The knit may be obtained on a warp knitting machine or Raschel knitting machine. For example, the area of the face of the knit provided with the barbs and the loops may show columns of loops alternating with columns of barbs. Alternatively, the loops and the barbs may be randomly distributed in the area.

In embodiments, the loops and the barbs define looped zones and barbed zones organised according to patterns selected from stripes, concentric circles, concentric rectangles, concentric squares, quincunx, and combinations thereof.

The barbs may be obtained by melting loops generated by a heat-fusible monofilament yarn used in the knitting process. In such a case, the barbs have the shape of a shaft, having the diameter of the yarn used for their formation, surmounted by a head having a diameter greater than that of the shaft. The generation of barbs from preliminary loops made of heat-fusible monofilament yarn is known and is described, for example in document WO 01/81667.

In embodiments, the heat-fusible monofilament yarn used in the knitting process to form the barbs is made of a bioresorbable material. For example, the heat-fusible monofilament yarn is a polylactic acid monofilament yarn having a diameter of 0.15 mm: such a yarn having such a diameter makes it possible to obtain barbs that have good anchoring abilities in biological tissues or in another openwork textile. Alternatively, the heat-fusible monofilament yarn may be a polylactic acid monofilament yarn having a diameter of 0.12 mm.

Another aspect of the invention is a process for manufacturing a surgical textile comprising a first face and a second face, opposite the first face, comprising the following steps:
A) knitting, on a Raschel knitting machine or a warp knitting machine: one or more several yarns according to a knitting pattern allowing the formation of said first and second faces of the textile and at least one heat-fusible monofilament yarn according to a knitting pattern allowing the formation of loops protruding outwards said first face on at least an area of the surface of said first face, said loops showing a length L2, measured perpendicularly to said surface,
B) cutting, by melting, some of the loops formed at step A), each cut loop thus generating two barbs, each barb showing a length L1, measured perpendicularly to said surface, wherein L2 is greater than L1.

The cutting of step B) may be performed by contacting the loops with a cylinder that is brought to a temperature that causes the loops to melt so that they are cut in two and thus form the barbs, as described in WO01/81667. This cutting generates two barbs, each of them having a head with dimensions usually greater than its shaft.

In embodiments, step B) is performed by heating a press to a temperature that causes the loops to melt and applying said heated press on said first face of the knit, said press being shaped and dimensioned so that only some of the loops are contacted by said press and are thus caused to melt.

In embodiments, two different heat-fusible monofilament yarns are used in step A) of the process above, a first heat-fusible monofilament yarn having a first diameter and generating first loops, and a second heat-fusible monofilament yarn having a second diameter and generating second loops, and only the first loops are cut by melting during step B).

In embodiments, the first diameter is greater than the second diameter. Such a process allows obtaining a surgical textile in which the barbs show a greater diameter than the loops. The force to apply to anchor the barbs into a biological tissue or other fabric may be moderate. In addition, the barbs may show a significant strength or rigidity while the loops show a moderate spring effect. The risk that the textile uplifts due to the presence of the loops is therefore reduced. The activation of the barbs is facilitated since the force necessary to reduce/flatten the loops may be reduced.

In alternative embodiments, the second diameter is greater than the first diameter. Such a process allows obtaining a surgical textile in which the loops show a greater diameter than the barbs. Such loops show a certain stiffness that ensures that the barbs are prevented from gripping to the biological tissues before the surgeon actually decides it. The deactivation of the barbs is therefore particularly efficient, and the barbs do not penetrate the tissue or another fabric before the surgeon decides to apply the necessary pressure on the textile.

Suitable knitting patterns for the process above are described below.

The knit may be produced on a warp knitting machine having four guide bars B1, B2, B3 and B4, where B1 is unthreaded, and B2, B3 and B4 are threaded according to the following knitting pattern, according to the ISO 11676 standard (publication year 2014):
Bar B2: 1.0/0.1//
Bar B3: 1.0/5.5/1.0/3.3//
Bar B4: 2.1/5.5/3.4/0.0//
where the yarns threaded in guide bars B2 and B3 are monofilament yarns of polyester terephthalate (PET) having a diameter of 0.09 mm and form the first and second faces of the textile, and the yarn threaded in guide bar B4 is a heat-fusible monofilament yarn, for example a polylactic acid monofilament yarn, and produces the loops.

Alternatively, the knit may be produced on a warp knitting machine having four guide bars B1, B2, B3 and B4, where B1 is unthreaded, and B2, B3 and B4 are threaded according to the following knitting pattern, according to the ISO 11676 standard (publication year 2014):

Bar B2: 1.0/0.1//
Bar B3: 1.0/7.7/6.6/7.7//
Bar B4: 2.1/5.5/3.4/0.0// where the yarns threaded in guide bars B2 and B3 are monofilament yarns of polyester terephthalate (PET) having a diameter of 0.09 mm and form the first and second faces of the textile, and the yarn threaded in guide bar B4 is a heat-fusible monofilament yarn, for example a polylactic acid monofilament yarn, and produces the loops.

Alternatively, the knit may be produced on a warp knitting machine with four guide bars B1, B2, B3 and B4, according to the following knitting pattern according to the standard ISO 11676 (publication year 2014):

B2: 0-1/3-4/7-6/4-3/0-1/2-1//
B3: 7-6/4-3/0-1/3-4/7-6/5-6//
B4: 4-4/1-2/0-1/2-1/4-4/2-2// where B1 is unthreaded.

The knitting patterns of the process above may produce openwork faces for the textile, such open work faces favouring cell recolonization. In the present application, the expression "openwork face" is understood to mean that said face comprises openings or pores: these openings or pores are in particular generated by the knitting pattern followed for the knitting of the yarns in the process above, and may correspond to the various meshes of said knit.

The surgical textile according to the invention can be used as is in order to constitute a reinforcing prosthesis for repairing a hernia, or it may constitute one part of a reinforcing prosthesis for repairing hernias.

Thus, when the surgeon wishes to implant a prosthesis formed of a surgical textile according to the invention, he can easily roll the textile up on itself: since the loops are longer than the barbs, they will protect the barbs and prevent them from gripping the textile.

It is then possible to introduce the textile according to the invention, thus rolled up, into a trocar, for example having an internal diameter of 10 mm. Once the surgical textile according to the invention has been thus conveyed in the form of a roll to the implantation site via the trocar, it can be unrolled and deployed easily: the barbs have not gripped the textile, and the textile can therefore be deployed easily.

The surgical textile can also be conveyed to the surgical site directly through the surrounding tissues, via open surgery, without damaging the tissues.

The textile can then be fastened either to another fabric, or to a biological wall, owing to the anchoring abilities of the barbs, by applying a pressure to the textile, to flatten the loops and activate the barbs.

In embodiments, the two faces of the textile may be provided with areas having a plurality of loops and a plurality of barbs.

The invention will be better understood from the following detailed description and figures, in which.

Figure 1A:
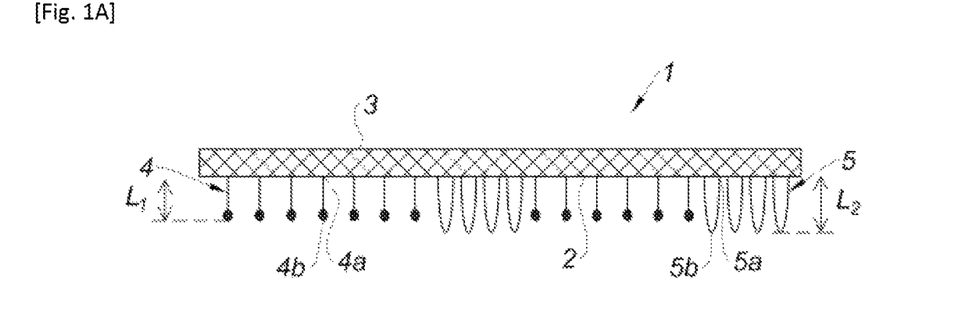
FIG. 1A is a schematic cross section view of a first embodiment of a textile according to the invention.

With reference to FIG. 1A is shown a surgical textile 1 according to the invention. The surgical textile 1 has a first face 2 and a second face 3, opposite the first face 2. The textile 1 comprises an arrangement of yarns forming the background of the textile 1 and defining said first face 2 and second face 3.

As appears from FIG. 1A, the first face 2 is provided with a plurality of barbs 4 and with a plurality of loops 5. The barbs 4 have a foot 4a and a head 4b. The loops 5 have a basis 5a and an apex 5b.

In FIG. 1A, the barbs 4 and the loops 5 extend substantially perpendicularly with respect to the surface of the first face 2: the length L1 of a barb 4, measured perpendicularly to said surface, corresponds therefore to the length of the barb 4 between its foot 4a and its head 4b measured according to a longitudinal axis of the barb 4, and the length L2 of a loop 5, measured perpendicularly to said surface, corresponds therefore to the length of the loop 5 between its basis 5a and its apex 5b measured according to a longitudinal axis of the loop 5.

As can be seen from FIG. 1A, the length L2 is greater than the length L1.

For example, L1 may range from 0.5 mm to 1.0 mm, preferably from 0.7 mm to 0.9 mm, and L2 may range from 0.8 mm to 1.2 mm, preferably from 0.9 mm to 1.1 mm.

The loops 5 of the textile 1 allow protecting the barbs 4 when the textile 1 is conveyed to an implantation site. During the time the textile 1 is moved within the surrounding tissues, the loops 5 prevent the barbs 4 to anchor into the tissues.

Figure 1B:
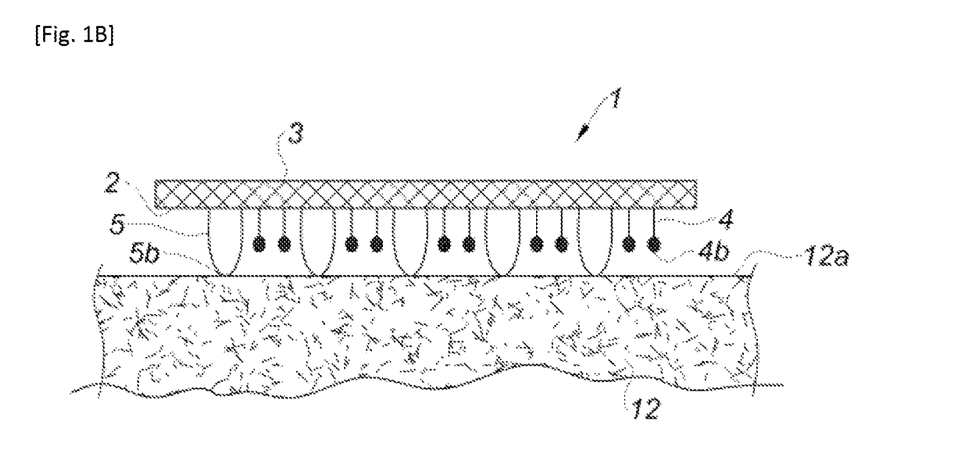
FIG. 1B is a schematic cross section view of a second embodiment of a textile of the invention with its face provided with barbs and loops facing a biological tissue.
Figure 1C:
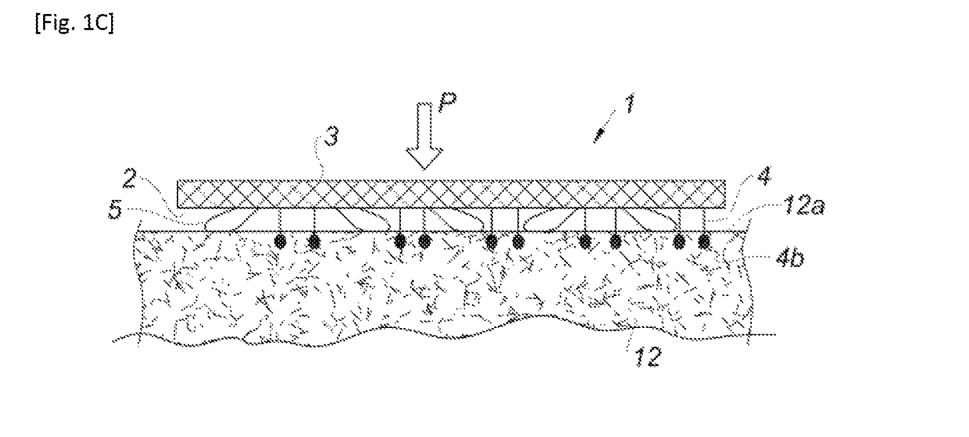
FIG. 1C is a schematic cross section view of the textile and biological tissue of FIG. 1B once the surgeon has applied a pressure to the textile to anchor it to the biological tissue.

FIGS. 1B and 1C are schematic cross section views of a textile 1 similar to that of FIG. 1A, at the vicinity of a biological tissue 12, when the textile 1 is being conveyed to the implantation site and the barbs 4 are deactivated, and further on when the textile 1 is being anchored to the biological tissue 12 by activation of the barbs 4.

As appears from FIG. 1B, when the textile 1 is moved within the patient's body up to the implantation site, the apexes 5b of the loops 5 are in contact with the outer surface 12a of the biological tissue 12. In the absence of any additional pressure other than the intrinsic abdominal wall pressure, the loops 5 thereby maintain the outer surface 12a of the biological tissue 12 away from the heads 4b of the barbs 4. The barbs 4 are therefore protected, their gripping function is deactivated, and the transport of the textile 1 up to the implantation site is facilitated, as the barbs 4 are prevented from anchoring into the biological tissue 12.

Once at the implantation site, the textile 1 is positioned so that its first face 2, provided with the barbs 4 and the loops 5, faces the outer surface 12a of the biological tissue 12 to which the textile 1 is intended to be fixed.

With reference to FIG. 1C, the surgeon may then apply a pressure, shown by an arrow P on this Figure, on top of the second face 3 of the textile 1. The pressure applied on the second face 3 of the textile 1 in the direction of the biological tissue 12 causes the loops 5 to flatten, and the barbs 4 to contact the outer surface 12a of the biological tissue and enter into the biological tissue 12. The heads 4b of the barbs 4 are then able to grip the biological tissue 12. The gripping function of the barbs 4 is activated.

The textile 1 allows therefore deactivating the barbs 4 during the time the textile 1 is conveyed to the implantation site, either through surrounding tissues, or in a folded or rolled configuration of the textile 1 in a trocar, and activating the barbs 4 when needed.

Figure 1D:
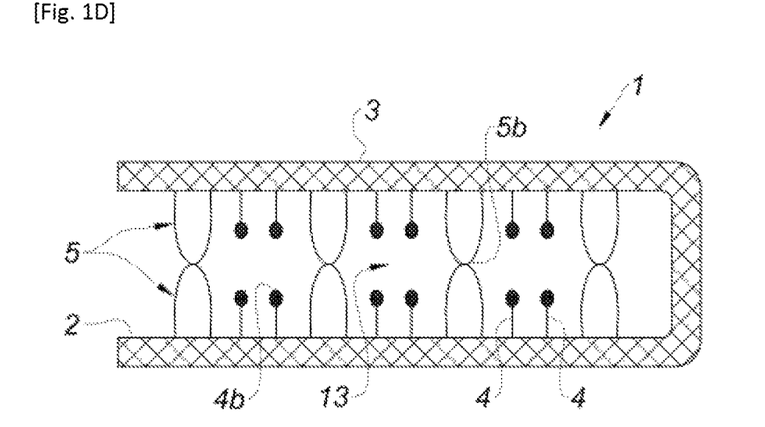
FIG. 1D is a schematic cross section view of the textile of FIG. 1B, which has been folded on itself.

With reference to FIG. 1D is shown the textile 1 of FIGS. 1B-1C in a configuration in which the textile 1 is folded on itself. As appears on this Figure, when the textile 1 is folded on itself, the respective apexes 5b of two loops 5 facing each other contact themselves, thereby maintaining a safety space 13 between the heads 4b of two barbs 4 facing each other. The barbs 4 are therefore protected and deactivated, and they are prevented from becoming entangled with each other as well as with the background of the textile 1.

Figure 1E:
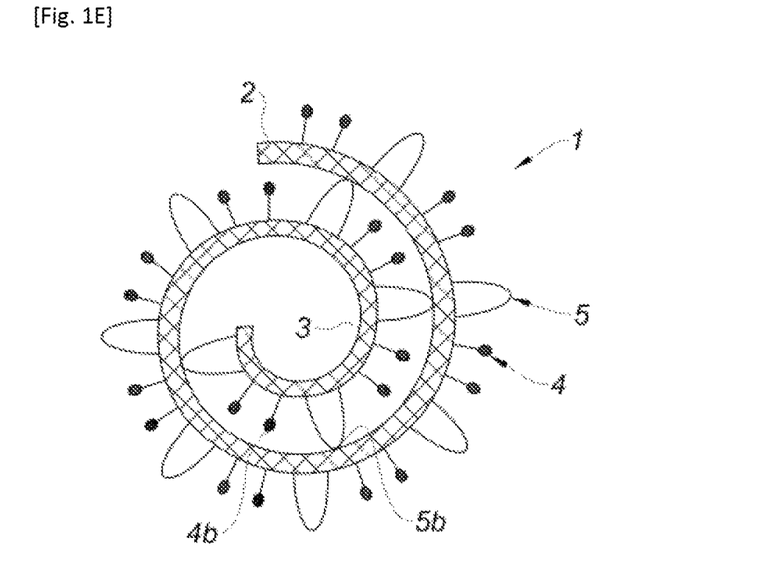
FIG. 1E is a schematic cross section view of the textile of FIG. 1B, which has been rolled on itself.

With reference to FIG. 1E is shown the textile 1 of FIGS. 1B-1D in a configuration in which it has been rolled on itself, for example for introduction inside a trocar. As appears on this Figure, when the textile 1 is rolled on itself, the apexes 5b of the loops 5 contact the second face 3 of the textile 1, thereby maintaining the barbs 4, and in particular their heads 4b, away from this second face 3 of the textile 1. The barbs 4 are therefore protected and deactivated, and prevented from becoming entangled in the background of the textile 1.

The deactivation of the barbs 4, as described above during the transport of the textile 1 within patient's body, also allows an easier deployment of the textile 1 once it has reached the implantation site. The deactivation of the barbs 4 by the loops 5 also allows the textile 1 to be detached and re-attached easily on the implantation site, so that the surgeon may reposition the textile 1 in order to fix it in the best position.

Figure 2:
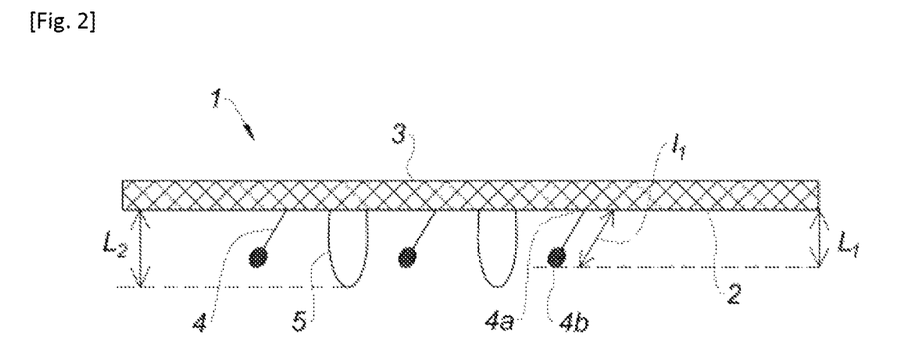
FIG. 2 is a schematic cross section view of a third embodiment of a textile according to the invention.

FIG. 2 is a schematic view of a textile 1 similar to that of FIG. 1A, in which the barbs 4 extend obliquely with respect to the surface of the first face 2. In such a case, the length l1 of a barb 4 between its foot 4a and its head 4b along a longitudinal axis of the barb 4 is longer than the length L1 of the barb 4, measured perpendicularly to the surface of the first face 2. As shown on this Figure, in any case, L2 is greater than L1, and the loops 5 can assume their protective function of the barbs 4.

Figure 3:
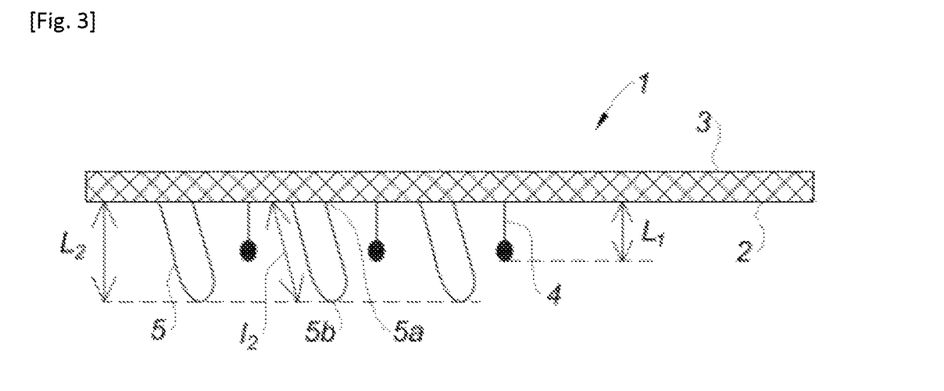
FIG. 3 is a schematic cross section view of a fourth embodiment of a textile according to the invention.

FIG. 3 is a schematic view of a textile 1 similar to that of FIG. 1A, in which the loops 5 extend obliquely with respect to the surface of the first face 2. In such a case, the length l2 of a loop 5 between its basis 5a and its head 5b along a longitudinal axis of the loop 5 is longer than the length L2 of the loop 5, measured perpendicularly to the surface of the first face 2. As shown on this Figure, in any case, L2 is greater than L1, and the loops 5 can assume their protective function of the barbs 4.

Figure 4:
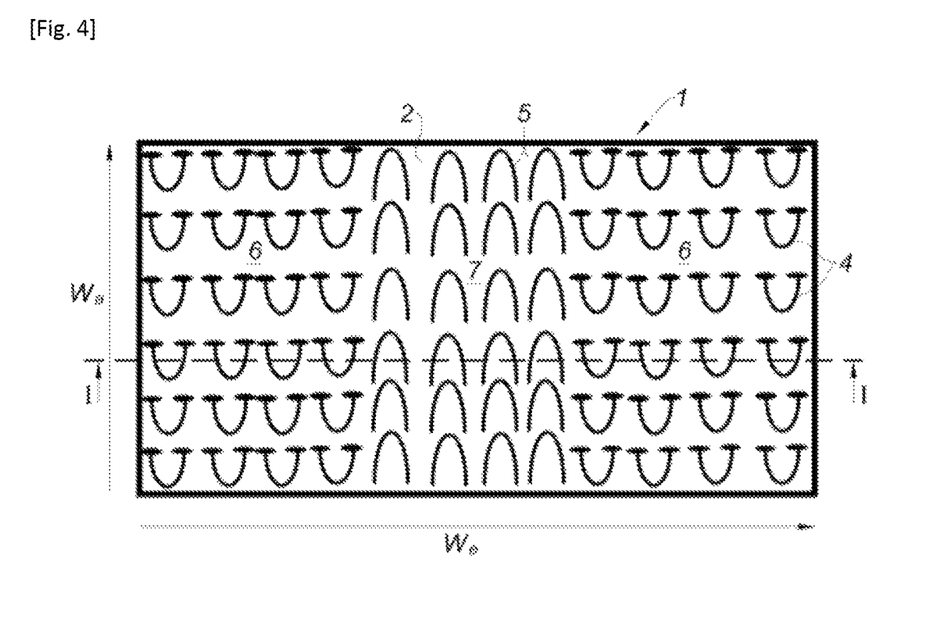
FIG. 4 is a schematic top view of the face of the textile of the invention, in which the looped zones and the barbed zones are organised according to a pattern forming stripes.
Figure 5:
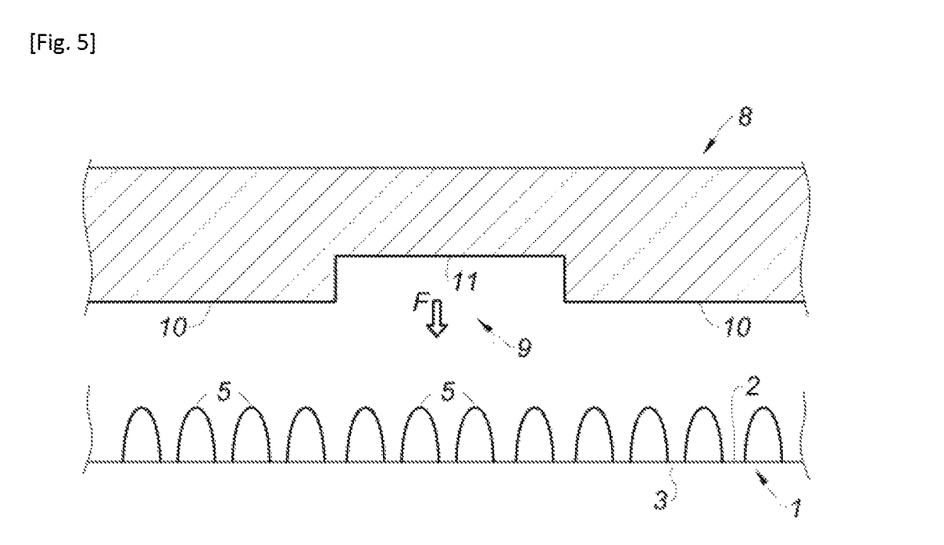
FIG. 5 is a schematic cross section view along plane I-I of the textile of FIG. 4 before the melting step of the loops and of the press used for the melting step.

FIG. 4 is a top perspective view of a textile 1 similar to that of FIG. 1A, in which the barbs 4 form barbed zones 6 and the loops 5 form looped zones 7. The textile 1 of FIG. 4 is a knit and FIG. 4 indicates the weft (We) direction and the warp (Wa) direction of the textile 1. As appears from this Figure, the barbed zones 6 alternate with the looped zones 7 according to vertical bands, thereby defining a pattern forming stripes. With reference to FIG. 5, the textile 1 of FIG. 4 may be obtained by first knitting one or more several yarns according to a knitting pattern forming the first 2 and the second faces of the textile 1 and one heat-fusible monofilament yarn according to a knitting pattern allowing the formation of the loops 5 protruding outwards the first face 2.

In a second step, a press 8, shaped and dimensioned so as to show a specific relief 9, is heated to a temperature that causes the loops 5 to melt and is moved towards the first face 2 of the textile 1 according to arrow F shown on FIG. 5. The relief 9 of the press 8 shows protruding portions 10 and recessed portions 11 (only one being visible on FIG. 5). The press 8 is moved until the protruding portions 10 contact and melt the loops 5 facing said protruding portions 10, while the recessed portions 11 remain away from the loops 5. The melt loops 5 give rise to the barbs 4 as shown in FIG. 4, while the uncontacted loops 5 remain unchanged. The textile 1 of FIG. 4 is obtained.

Figure 6:
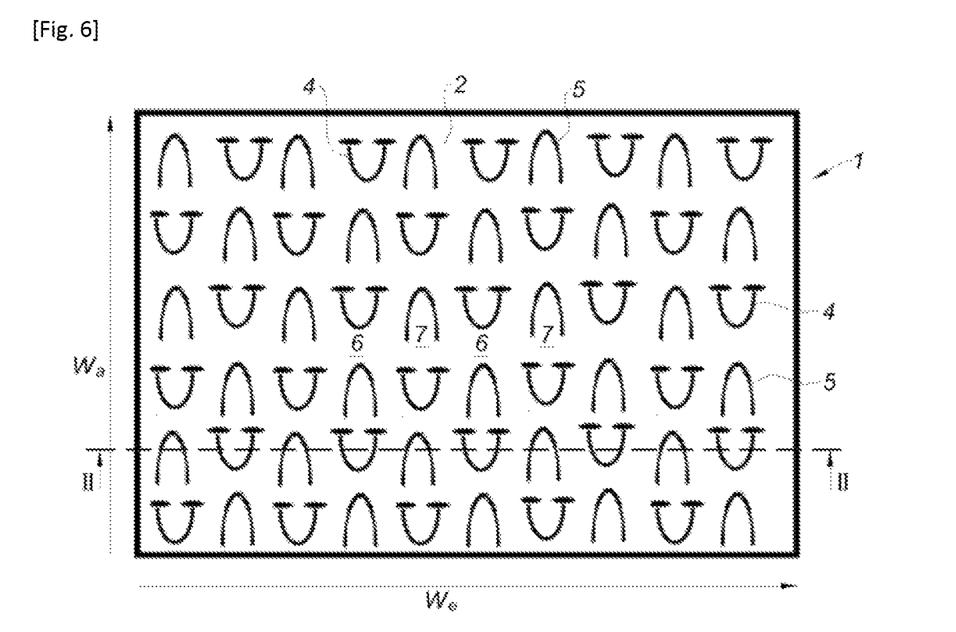
FIG. 6 is a schematic top view of the face of the textile of the invention, in which the looped zones and the barbed zones are organised according to a pattern forming a quincunx.
Figure 7:
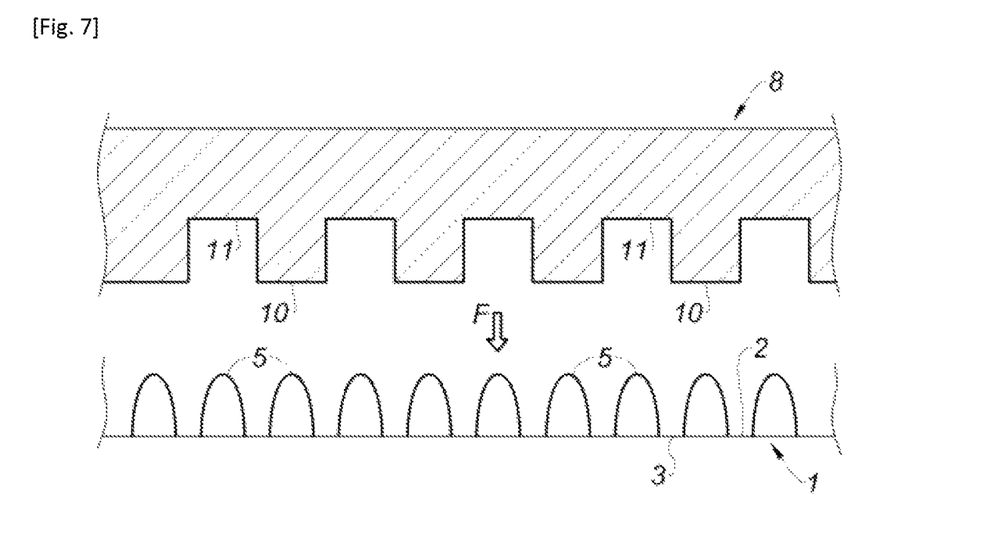
FIG. 7 is a schematic cross section view along plane II-II of the textile of FIG. 6 before the melting step of the loops and of the press used for the melting step.

FIGS. 6 and 7 illustrate a knitted textile 1 similar to that of FIGS. 4 and 5, in which the barbed zones 6 and the looped zones 7 are organised according to a quincunx pattern. The knitted textile 1 may be obtained as described in FIG. 4.

As appears from FIG. 7, the relief 9 of the press 8 is provided with protruding portions 10 and recessed portions 11 which are positioned according to a quincunx pattern. As described for FIGS. 4 and 5, the press 8 is heated to a temperature that causes the loops 5 to melt and is moved towards the first face 2 of the textile 1 until the protruding portions 10 contact and melt the loops 5 they face while the recessed portions 11 remain away from the loops 5 they face. The textile 1 of FIG. 6 is obtained.

Figure 8:
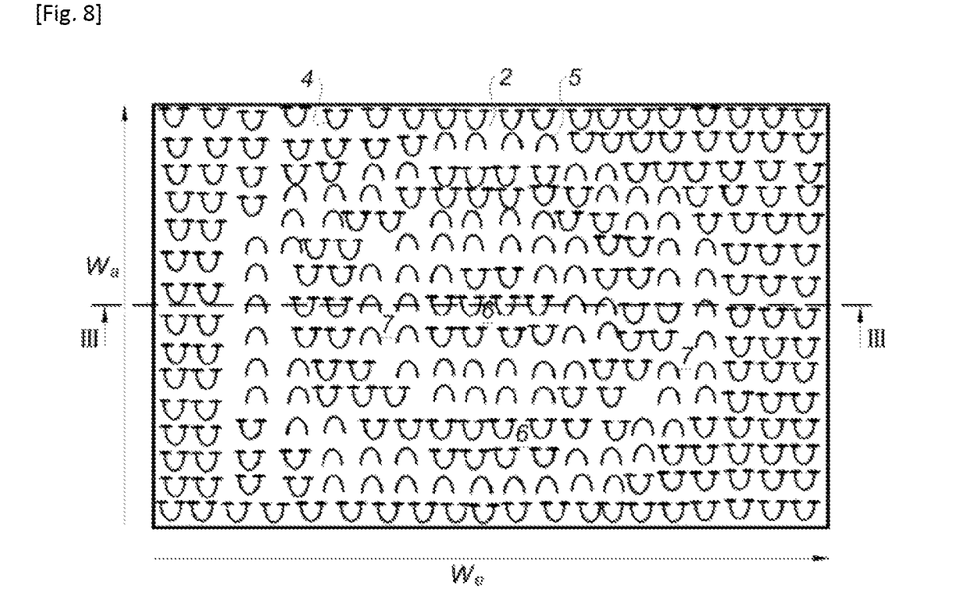
FIG. 8 is a schematic top view of the face of the textile of the invention, in which the looped zones and the barbed zones are organised according to a pattern forming concentric circles.
Figure 9:
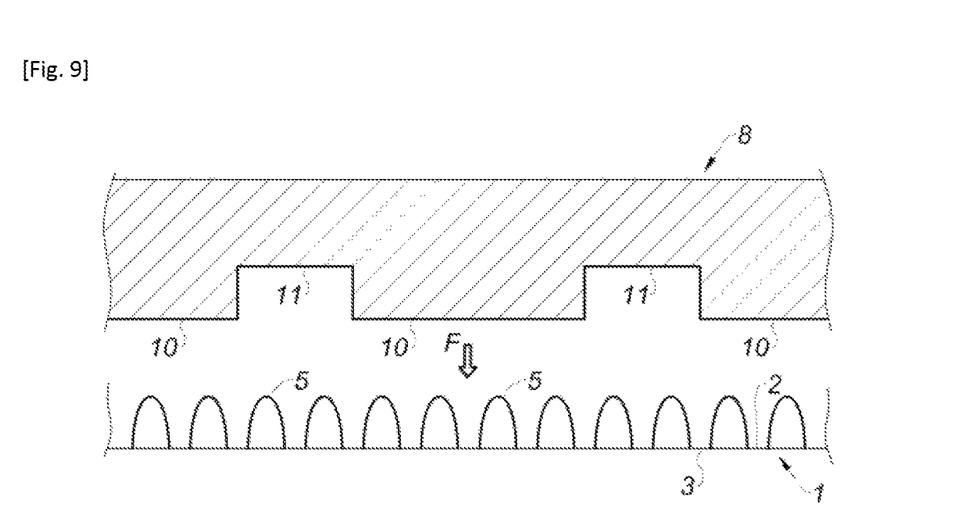
FIG. 9 is a schematic cross section view along plane of the textile of FIG. 8 before the melting step of the loops and of the press used for the melting step.

FIGS. 8 and 9 illustrate a knitted textile 1 similar to that of FIGS. 4 and 5, in which the barbed zones 6 and the looped zones 7 are organised according to a pattern defining concentric circles. The knitted textile 1 may be obtained as described in FIG. 4.

As appears from FIG. 9, the relief 9 of the press 8 is provided with protruding portions 10 and recessed portions 11 which are positioned according to a pattern defining concentric circles. As described for FIGS. 4 and 5, the press 8 is heated to a temperature that causes the loops 5 to melt and is moved towards the first face 2 of the textile 1 until the protruding portions 10 contact and melt the loops 5 they face while the recessed portions 11 remain away from the loops 5 they face. The textile 1 of FIG. 8 is obtained.

Figure 10:
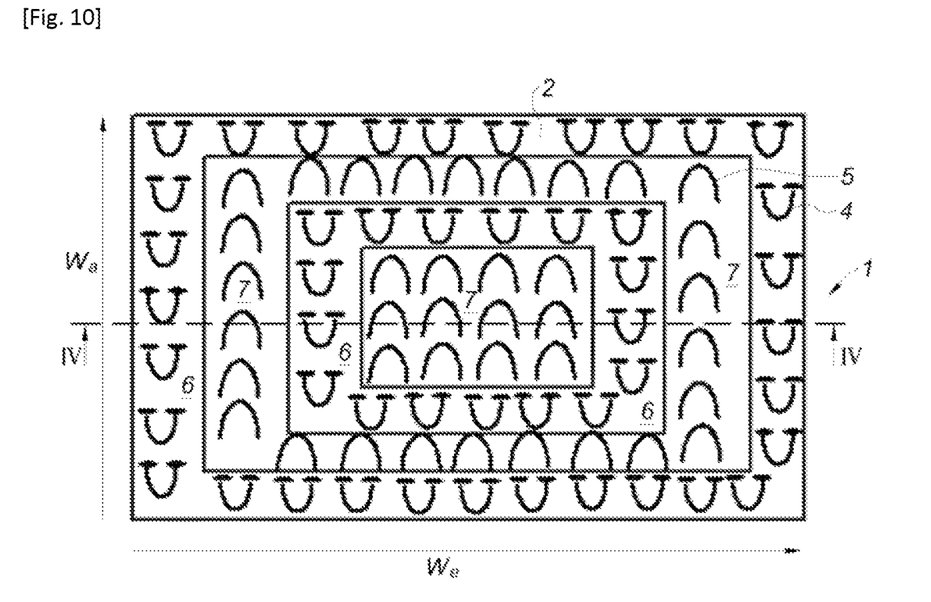
FIG. 10 is a schematic top view of the face of the textile of the invention, in which the looped zones and the barbed zones are organised according to a pattern forming concentric rectangles.
Figure 11:
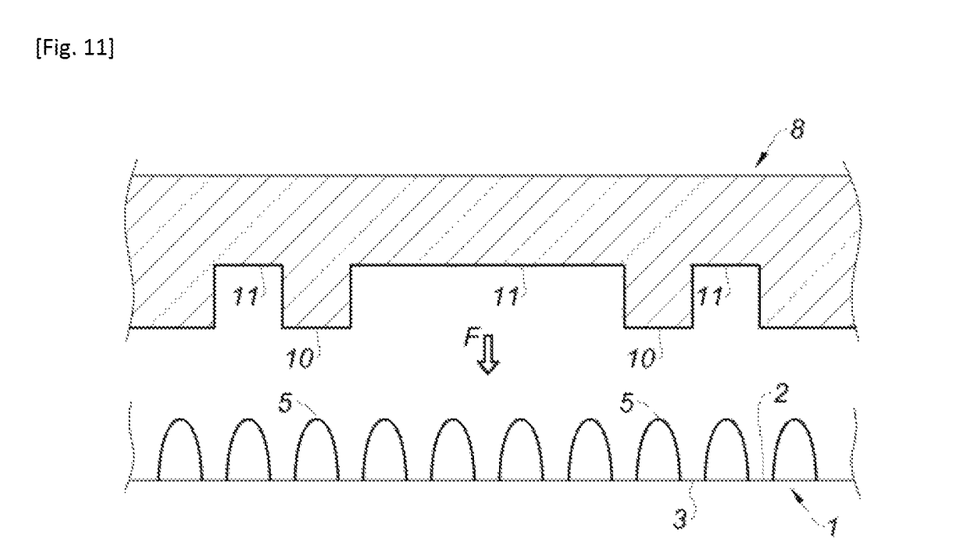
FIG. 11 is a schematic cross section view along plane IV-IV of the textile of FIG. 10 before the melting step of the loops and of the press used for the melting step.

FIGS. 10 and 11 illustrate a knitted textile 1 similar to that of FIGS. 4 and 5, in which the barbed zones 6 and the looped zones 7 are organised according to a pattern defining concentric rectangles. The knitted textile 1 may be obtained as described in FIG. 4.

As appears from FIG. 11, the relief 9 of the press 8 is provided with protruding portions 10 and recessed portions 11 which are positioned according to a pattern defining concentric rectangles. As described for FIGS. 4 and 5, the press 8 is heated to a temperature that causes the loops 5 to melt and is moved towards the first face 2 of the textile 1 until the protruding portions 10 contact and melt the loops 5 they face while the recessed portions 11 remain away from the loops 5 they face. The textile 1 of FIG. 10 is thus obtained.

EXAMPLES

Example 1

Surgical textiles have been prepared using one of the two following knitting patterns:
Knitting pattern A:
Bar B1: unthreaded
Bar B2: 1.0/0.1//
Bar B3: 1.0/5.5/1.0/3.3//
Bar B4: 2.1/5.5/3.4/0.0//
Knitting Pattern B:
Bar B1: unthreaded
Bar B2: 1.0/0.1//
Bar B3: 1.0/7.7/6.6/7.7//
Bar B4: 2.1/5.5/3.4/0.0//

Five surgical textiles of the invention have been prepared as follows:

KNIT 1: this knit was prepared using Knitting pattern A, with bars B2 and B3 being threaded with monofilament yarns of polyester terephthalate (PET) having a diameter of 0.08 mm. Bar B4 was threaded with a first heat-fusible monofilament yarn of polylactic acid having a diameter of 0.12 mm producing first loops and with a second heat-fusible monofilament yarn of polylactic acid having a diameter of 0.15 mm producing second loops.

The first loops and the second loops were distributed according to vertical bands. During the cutting step as described above in the application, only the second loops were melt and cut, giving rise to barbs, according to the process step shown in FIG. 5.

The present knit therefore shows looped zones and barbed zones organised according to a pattern forming stripes similar to that shown in FIG. 4. In addition, the diameter of the barbs is greater than the diameter of the loops.

KNIT 2: this knit was prepared using Knitting pattern A, with bars B2 and B3 being threaded with monofilament yarns of polyester terephthalate (PET) having a diameter of 0.08 mm. Bar B4 was threaded with a first heat-fusible monofilament yarn of polylactic acid having a diameter of 0.15 mm producing first loops and with a second heat-fusible monofilament yarn of polylactic acid having a diameter of 0.12 mm producing second loops.

The first loops and the second loops were distributed according to vertical bands. During the cutting step as described above in the application, only the second loops were melt and cut, giving rise to barbs, according to the process step shown in FIG. 5.

The present knit therefore shows looped zones and barbed zones organised according to a pattern forming stripes similar to that shown in FIG. 4. In addition, the diameter of the loops is greater than the diameter of the barbs.

KNIT 3: this knit was prepared using Knitting pattern A, with bars B2 and B3 being threaded with monofilament yarns of polyester terephthalate (PET) having a diameter of 0.09 mm. Bar B4 was threaded with a first heat-fusible monofilament yarn of polylactic acid having a diameter of 0.15 mm producing first loops and with a second heat-fusible monofilament yarn of polylactic acid having a diameter of 0.12 mm producing second loops.

The first loops and the second loops were distributed according to vertical bands. During the cutting step as described above in the application, only the second loops were melt and cut, giving rise to barbs, according to the process step shown in FIG. 5.

The present knit therefore shows looped zones and barbed zones organised according to a pattern forming stripes similar to that shown in FIG. 4. In addition, the diameter of the loops is greater than the diameter of the barbs.

KNIT 4: this knit was prepared using Knitting pattern A, with bars B2 and B3 being threaded with monofilament yarns of polyester terephthalate (PET) having a diameter of 0.09 mm. Bar B4 was threaded with a first heat-fusible monofilament yarn of polylactic acid having a diameter of 0.12 mm producing first loops and with a second heat-fusible monofilament yarn of polylactic acid having a diameter of 0.15 mm producing second loops.

The first loops and the second loops were distributed according to vertical bands. During the cutting step as described above in the application, only the second loops were melt and cut, giving rise to barbs, according to the process step shown in FIG. 5.

The present knit therefore shows looped zones and barbed zones organised according to a pattern forming stripes similar to that shown in FIG. 4. In addition, the diameter of the barbs is greater than the diameter of the loops.

KNIT 5: this knit was prepared using Knitting pattern B, with bars B2 and B3 being threaded with monofilament yarns of polyester terephthalate (PET) having a diameter of 0.09 mm. Bar B4 was threaded with a heat-fusible monofilament yarn of polylactic acid having a diameter of 0.15 mm producing loops.

During the cutting step as described above in the application, a press having a quincunx shaped relief was used, as shown in FIG. 7. As a result, one out of two loops is melt and cut, giving rise to barbs.

The present knit therefore shows looped zones and barbed zones organised according to a quincunx pattern similar to that shown in FIG. 6. In addition, the diameter of the barbs is the same as the diameter of the loops.

Two comparative textiles have been prepared as follows:
KNIT 6: this knit was prepared using Knitting pattern A, with bars B2 and B3 being threaded with monofilament yarns of polyester terephthalate (PET) having a diameter of 0.08 mm. Bar B4 was threaded with a heat-fusible monofilament yarn of polylactic acid having a diameter of 0.15 mm producing loops.

The cutting step was performed by contacting all the loops with a cylinder brought to a temperature causing all the loops to melt as described in WO01/81667. As a result, all the loops were cut and gave rise to barbs.

The present comparative knit is therefore provided with barbs only and is free of loops.

KNIT 7: this knit was prepared using Knitting pattern B, with bars B2 and B3 being threaded with monofilament yarns of polyester terephthalate (PET) having a diameter of 0.09 mm. Bar B4 was threaded with a heat-fusible monofilament yarn of polylactic acid having a diameter of 0.15 mm producing loops.

The cutting step was performed by contacting all the loops with a cylinder brought to a temperature causing all the loops to melt as described in WO01/81667. As a result, all the loops were cut and gave rise to barbs.

The present comparative knit is therefore provided with barbs only and is free of loops.

The "gripping-on-itself" properties of the seven knits above were evaluated according to the following protocol: knit samples of 30 cm×5 cm (warp X weft) are prepared. Each knit sample is then folded once on itself, as shown in FIG. 1D, along the weft direction, so that the folded sample has the following dimensions: 15 cm×5 cm. The central part of the folded sample (10 cm×5 cm) is then submitted to a compaction by means of a mass being applied thereon 5 times, so that the barbs are forced to grip the background of the textile. The folded end of the sample is cut so that a compacted two-layered sample is obtained, where each layer of textile is intimately entangled with the other by means of the barbs gripping together and gripping the background of the textile. The sample is then positioned on a traction machine having a fixed jaw and a mobile jaw. At one end of the sample, the end of the first layer is attached to the fixed jaw and the end of the second layer is attached to the mobile jaw. The machine is set up with the following parameters: distance between the jaws is 3 cm, preload is 0 Newton, extension speed is 100 mm/min, the force is set to 0 before testing.

The maximal force (in Newton) necessary for separating the two layers is measured. This maximal force (N) corresponds to the "gripping on itself" property of the tested knit.

Figure 12:
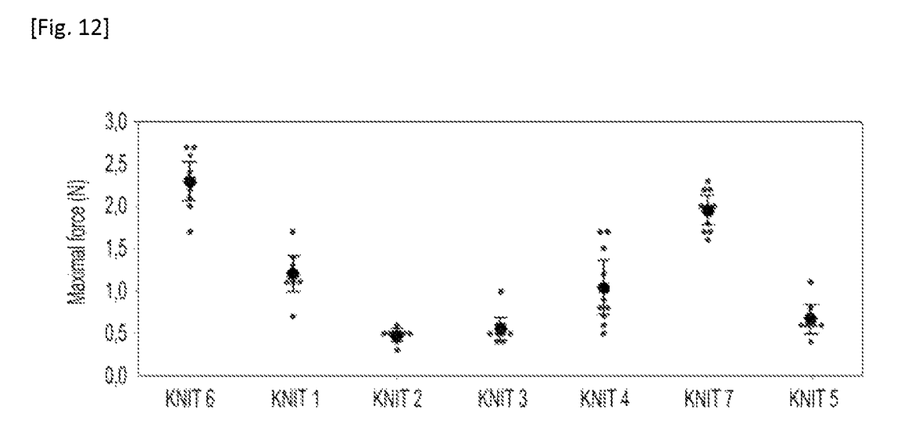
FIG. 12 is a graph showing the self-gripping properties of textiles of the invention and of comparative textiles.

The results are shown in FIG. 12.

As appears from this Figure, the textiles of the invention, namely KNITS 1 to 5, show a maximal force lower than the comparative textiles KNIT 6 and KNIT 7. This means that the textiles of the invention show less gripping forces on itself than the comparative textiles.

The deployment of the surgical textile of the invention in the surgical site is therefore improved, as the barbs of the textiles of the invention are less plugged into the background of the textile than that of the comparative textiles, and are therefore easy to detach when the surgeon wishes to unfold the textile.

In particular, thanks to the presence of the loops in the textiles of the invention, the barbs of the textiles of the invention are less entangled with one another and are less engaged in the pores of the background of the textile when the textile is folded on itself.

As a result, once at the implantation site, the unfolding of the textiles of the invention is facilitated compared to that of the comparative textiles. The exact positioning of the textiles of the invention is also improved, as the barbs are deactivated by the presence of the loops and they therefore do not impede the smooth conveying of the textiles. Thanks to the presence of the loops, the spreading of the textiles of the inventions is also made easier than for the comparative textiles. The surgeon may then push on the textile to flatten the loops and activate the barbs, so as to anchor the barbs to the biological tissue, as shown for example in FIG. 1C. In addition, the repositioning of the textiles of the invention is also rendered possible, due to their lower gripping-on-itself properties, which allows attaching and detaching the barbs to the biological tissue more easily.

Example 2

Textiles of the invention, in particular some knits of EXAMPLE 1 above, were tested and evaluated in a simulated use environment on a pig abdominal wall model, in a view to assess the ease of use of the textiles of the invention, in particular with regards to their "gripping to surrounding tissues" when said textiles are inserted.

For each knit referred to as KNIT 3, KNIT 4 and KNIT 5 of EXAMPLE 1, three samples were prepared.

The samples were folded in half, along the weft direction of the knit, with the barbs protruding outwards.

An incision was performed on the pig wall and each folded sample was inserted through the incision to a previously created surgical site.

Each sample was deployed and slight pressure was applied on the wall to simulate the intrinsic abdominal wall pressure.

Each sample was then removed by pulling it out of the created surgical site to assess the quantity of surrounding tissues trapped by the sample.

The results showed that the presence of barbs and loops improved:
  the insertion of the textile: the loops prevent the barbs from being in contact with the surrounding tissues during the insertion step,
  the deployment of the textile, in particular:
    the unfolding of the textile is facilitated by the low gripping on itself of the barbs of the textiles of the invention. The deployment of the textile on the surgical site is therefore easier with the textiles of the invention than with comparative textiles showing barbs only;
    The exact positioning of the textile at the surgical site is facilitated: the presence of both barbs and loops allows moving the textile within the surrounding tissues more smoothly, without damaging these surrounding tissues: see for example FIG. 1B showing that the surrounding tissues are not gripped by the barbs of the textile of the invention as long as the intrinsic abdominal pressure only is present,
    The spreading of the textile is made easier: the presence of both barbs and loops allows a wide deploying of the textile, as the barbs do not entangle with one another as the surgeon manipulates the textile to lay it down at the surgical site.

Moreover, thanks to the presence of both barbs and loops, the surgeon may easily attach and detach the textile to the biological tissues, several times if needed, thereby facilitating the repositioning of the textile.

The textile of the present invention allows providing a self-gripping surgical textile capable of being introduced in the body of the patient without damaging the barbs and/or the surrounding biological tissues.

The invention claimed is:

1. A surgical textile comprising an arrangement of biocompatible yarns defining a first face and a second face of the textile, the second face opposite the first face, the textile being provided at least on an area of a surface of one of its faces with a plurality of barbs showing substantially a first length, measured perpendicularly to that surface, characterized in that said area of said surface is further provided with a plurality of loops, said loops showing substantially a second length, measured perpendicularly to that surface, where the first length ranges from 0.5 mm to 1.0 mm and the second length is greater than the first length, wherein the barbs are made of a yarn having a first diameter and the loops are made of a yarn having a second diameter, where the first diameter is greater than the second diameter.

2. The surgical textile according to claim 1, wherein the second length is from 20% to 140% longer than the first length.

3. The surgical textile according to claim 1, wherein the second length ranges from 0.8 mm to 1.2 mm.

4. The surgical textile according to claim 1, wherein the first diameter is from 10% to 80% greater than the second diameter.

5. The surgical textile according to claim 1, wherein the first diameter ranges from 0.10 mm to 0.18 mm and the second diameter ranges from 0.09 mm to 0.17 mm.

6. The surgical textile according to claim 1, wherein the barbs are made of a biodegradable material.

7. The surgical textile according to claim 1, wherein the arrangement of yarns is a knit comprising i) one or more yarn(s) forming said first and second faces of said textile and said loops and ii) heat-fusible monofilament yarn cuts forming said barbs.

8. The surgical textile according to claim 1, wherein the loops and the barbs define looped zones and barbed zones organized according to patterns selected from stripes, concentric circles, concentric rectangles, concentric squares, quincunx, and combinations thereof.

9. A surgical textile comprising an arrangement of biocompatible yarns defining a first face and a second face of the textile, the second face opposite the first face, the textile being provided at least on an area of a surface of one of its faces with a plurality of barbs showing substantially a first length, measured perpendicularly to that surface, characterized in that said area of said surface is further provided with a plurality of loops, said loops showing substantially a second length, measured perpendicularly to that surface, where the first length ranges from 0.5 mm to 1.0 mm and the second length is greater than the first length, wherein the barbs are made of a yarn having a first diameter and the loops are made of a yarn having a second diameter, where the second diameter is greater than the first diameter.

10. The surgical textile according to claim 9, wherein the second diameter is from 10% to 80% greater than the first diameter.

11. The surgical textile according to claim 9, wherein the second diameter is from 15% to 40% greater than the first diameter.

12. The surgical textile according to claim 9, wherein the second diameter ranges from 0.10 mm to 0.18 mm and the first diameter ranges from 0.09 mm to 0.17 mm.

13. The surgical textile according to claim 9, wherein the barbs are made of a biodegradable material.

14. The surgical textile according to claim 9, wherein the arrangement of yarns is a knit comprising i) one or more yarn(s) forming said first and second faces of said textile and said loops and ii) heat-fusible monofilament yarn cuts forming said barbs.

15. The surgical textile according to claim 9, wherein the loops and the barbs define looped zones and barbed zones organized according to patterns selected from stripes, concentric circles, concentric rectangles, concentric squares, quincunx, and combinations thereof.

16. A surgical textile comprising an arrangement of biocompatible yarns defining a first face and a second face of the textile, the second face opposite the first face, the textile being provided at least on an area of a surface of one of its faces with a plurality of barbs showing substantially a first length, measured perpendicularly to that surface, characterized in that said area of said surface is further provided with a plurality of loops, said loops showing substantially a second length, measured perpendicularly to that surface, where the first length ranges from 0.5 mm to 1.0 mm and the second length is greater than the first length, wherein the barbs are made of heat-fusible monofilament yarn cuts.

17. The surgical textile according to claim 16, wherein the barbs are made of a biodegradable material.

18. The surgical textile according to claim 16, wherein the loops and the barbs define looped zones and barbed zones organized according to patterns selected from stripes, concentric circles, concentric rectangles, concentric squares, quincunx, and combinations thereof.

* * * * *